(12) United States Patent
Freeberg

(10) Patent No.: US 7,751,894 B1
(45) Date of Patent: Jul. 6, 2010

(54) SYSTEMS AND METHODS FOR INDICATING ABERRANT BEHAVIOR DETECTED BY AN IMPLANTED MEDICAL DEVICE

(75) Inventor: Scott M. Freeberg, Birchwood Village, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 146 days.

(21) Appl. No.: 10/837,851

(22) Filed: May 3, 2004

Related U.S. Application Data

(63) Continuation-in-part of application No. 10/793,177, filed on Mar. 4, 2004, now abandoned.

(51) Int. Cl.
*A61N 1/08* (2006.01)

(52) U.S. Cl. .......................................... 607/42

(58) Field of Classification Search ............... 607/60, 607/42, 14, 32, 30, 2, 4, 5, 9, 20, 62, 116; 128/103; 600/373, 374, 377, 483, 508, 509, 600/529, 532, 533
See application file for complete search history.

(56) References Cited

U.S. PATENT DOCUMENTS

| | | | | |
|---|---|---|---|---|
| 5,275,159 | A * | 1/1994 | Griebel | 600/324 |
| 5,485,850 | A * | 1/1996 | Dietz | 600/529 |
| 5,904,708 | A * | 5/1999 | Goedeke | 607/18 |
| 6,304,773 | B1 | 10/2001 | Taylor et al. | |
| 6,306,088 | B1 * | 10/2001 | Krausman et al. | 600/301 |
| 6,336,903 | B1 | 1/2002 | Bardy | |
| 6,368,284 | B1 | 4/2002 | Bardy | |
| 6,398,728 | B1 | 6/2002 | Bardy | |
| 6,411,840 | B1 | 6/2002 | Bardy | |
| 6,440,066 | B1 | 8/2002 | Bardy | |
| 6,466,810 | B1 | 10/2002 | Ward et al. | |

(Continued)

OTHER PUBLICATIONS

Massey, P. J.; "Fabric Antennas for Mobile Telephony Integrated within Clothing," Phillips Research Laboratories, Redhill, UK; 4 pages.

(Continued)

*Primary Examiner*—Carl H Layno
*Assistant Examiner*—Frances P Oropeza
(74) *Attorney, Agent, or Firm*—Hollingsworth & Funk, LLC

(57) ABSTRACT

Various systems and methods are provided for intervening where aberrant heart and/or respiratory functionality is detected. For example, some embodiments of the present invention provide a monitor capable of detecting the occurrence of various aberrant events, and in some cases for intervening in the event. In some cases, a pacemaker or some other medical device detects an abnormality, and an information signal indicating the detected abnormality is transmitted from the pacemaker to a bedside monitor or some other monitor associated with the patient. Based on the received information signal, the bedside monitor can deliver an appropriate therapy. Such a therapy can be, but are not limited to, the sounding of an audible alarm to awake the patient, and/or the programming of a medical device implanted in the patient. Further, in some cases, the detected aberrant behavior and/or events surrounding the aberrant behavior can be transmitted from the bedside monitor to a remote monitor. Information can be retrieved from the remote monitor by a clinician and used in real time, or at a later time to diagnose and/or treat the patient.

12 Claims, 9 Drawing Sheets

U.S. PATENT DOCUMENTS

| | | | |
|---|---|---|---|
| 6,574,511 B2 * | 6/2003 | Lee | 607/60 |
| 6,587,725 B1 * | 7/2003 | Durand et al. | 607/42 |
| 6,602,201 B1 | 8/2003 | Hepp et al. | |
| 6,609,023 B1 | 8/2003 | Fischell et al. | |
| 6,614,406 B2 | 9/2003 | Amundson et al. | |
| 6,622,043 B1 | 9/2003 | Kraus et al. | |
| 6,622,045 B2 | 9/2003 | Snell et al. | |
| 6,635,014 B2 | 10/2003 | Starkweather et al. | |
| 6,636,769 B2 | 10/2003 | Govari et al. | |
| 6,638,231 B2 | 10/2003 | Govari et al. | |
| 6,644,321 B1 | 11/2003 | Behm | |
| 6,644,322 B2 | 11/2003 | Webb | |
| 6,647,299 B2 | 11/2003 | Bourget | |
| 6,648,821 B2 | 11/2003 | Lebel et al. | |
| 6,648,823 B2 | 11/2003 | Thompson | |
| 6,650,941 B2 | 11/2003 | Ferek-Petric | |
| 6,650,944 B2 | 11/2003 | Goedeke | |
| 6,658,283 B1 | 12/2003 | Bornzin et al. | |
| 6,658,300 B2 | 12/2003 | Govari et al. | |
| 6,752,765 B1 * | 6/2004 | Jensen et al. | 600/536 |
| 6,811,537 B2 | 11/2004 | Bardy | |
| 2001/0007053 A1 | 7/2001 | Bardy | |
| 2001/0029321 A1 | 10/2001 | Beetz et al. | |
| 2002/0013613 A1 | 1/2002 | Haller et al. | |
| 2002/0019586 A1 | 2/2002 | Teller et al. | |
| 2002/0019606 A1 | 2/2002 | Lebel et al. | |
| 2002/0026223 A1 | 2/2002 | Riff et al. | |
| 2002/0058906 A1 | 5/2002 | Lebel et al. | |
| 2002/0065454 A1 | 5/2002 | Lebel et al. | |
| 2002/0065509 A1 | 5/2002 | Lebel et al. | |
| 2002/0065539 A1 | 5/2002 | Von Arx et al. | |
| 2002/0065540 A1 | 5/2002 | Lebel et al. | |
| 2002/0072783 A1 | 6/2002 | Goedeke et al. | |
| 2002/0077553 A1 | 6/2002 | Govari et al. | |
| 2002/0077671 A1 | 6/2002 | Govari et al. | |
| 2002/0077672 A1 | 6/2002 | Govari et al. | |
| 2002/0077673 A1 | 6/2002 | Penner et al. | |
| 2002/0082665 A1 | 6/2002 | Haller et al. | |
| 2002/0087203 A1 | 7/2002 | Schmitt et al. | |
| 2002/0091416 A1 | 7/2002 | Wassmund et al. | |
| 2002/0099412 A1 | 7/2002 | Fischell et al. | |
| 2002/0099424 A1 | 7/2002 | Ferek-Petric | |
| 2002/0103514 A1 | 8/2002 | Abrahamson | |
| 2002/0111539 A1 | 8/2002 | Cosentino et al. | |
| 2002/0116032 A1 | 8/2002 | Ferek-Petric | |
| 2002/0123672 A1 | 9/2002 | Christophersom et al. | |
| 2002/0123673 A1 | 9/2002 | Webb et al. | |
| 2002/0123776 A1 | 9/2002 | Von Arx et al. | |
| 2002/0126036 A1 | 9/2002 | Flaherty et al. | |
| 2002/0143372 A1 | 10/2002 | Snell et al. | |
| 2002/0147388 A1 | 10/2002 | Mass et al. | |
| 2002/0151770 A1 | 10/2002 | Noll, III et al. | |
| 2002/0156504 A1 | 10/2002 | Chen et al. | |
| 2002/0173830 A1 | 11/2002 | Starkweather et al. | |
| 2002/0188215 A1 | 12/2002 | Ferek-Petric | |
| 2002/0188773 A1 | 12/2002 | Augustijn et al. | |
| 2002/0190905 A1 | 12/2002 | Flint et al. | |
| 2002/0193839 A1 | 12/2002 | Cho et al. | |
| 2002/0193846 A1 | 12/2002 | Pool et al. | |
| 2002/0198462 A1 | 12/2002 | Begemann | |
| 2003/0006898 A1 | 1/2003 | Herzberg | |
| 2003/0009204 A1 | 1/2003 | Amundson et al. | |
| 2003/0022637 A1 | 1/2003 | Hirota | |
| 2003/0023175 A1 | 1/2003 | Arzbaecher et al. | |
| 2003/0025645 A1 | 2/2003 | Amundson et al. | |
| 2003/0028226 A1 | 2/2003 | Thompson et al. | |
| 2003/0041866 A1 | 3/2003 | Linberg et al. | |
| 2003/0114896 A1 | 6/2003 | Boute et al. | |
| 2003/0114897 A1 | 6/2003 | Von Arx et al. | |
| 2003/0122718 A1 | 7/2003 | Fang et al. | |
| 2003/0139778 A1 | 7/2003 | Fischell et al. | |
| 2003/0144718 A1 | 7/2003 | Zeijlemaker | |
| 2003/0149423 A1 | 8/2003 | Fischell et al. | |
| 2003/0176933 A1 | 9/2003 | Lebel et al. | |
| 2003/0177031 A1 | 9/2003 | Malek | |
| 2003/0195396 A1 | 10/2003 | Scarantino et al. | |
| 2003/0195589 A1 | 10/2003 | Von Arx et al. | |
| 2003/0199939 A1 | 10/2003 | Schmitt et al. | |
| 2003/0204216 A1 | 10/2003 | Ries et al. | |
| 2003/0212441 A1 | 11/2003 | Starkweather et al. | |
| 2003/0216793 A1 | 11/2003 | Karlsson et al. | |
| 2003/0222823 A1 | 12/2003 | Flint et al. | |
| 2004/0122294 A1 * | 6/2004 | Hatlestad et al. | 600/300 |

OTHER PUBLICATIONS

Chen, Zhi Ning et al.; "A New Inverted F Antenna with a Ring Dielectric Resonator," IEEE Transactions on Vehicular Technology, vol. 48, No. 4, (Jul. 1999); pp. 1029-1032.

Hong, Wonbin; "Design of Small Inverted F Antenna for Low Frequencies," Department of Electrical and Computer Enginerring, Purdue University, 5 pages.

"Inverted F Antenna," http://www.qsl.net/kb7qhc/antenna/Inverted%20F; (Dec. 4, 2003); 2 pages.

"Film Type Inverted F Antenna," Honda Tsushin Kogyo Co., Ltd., Honda connectors; (Jun. 17, 2003); pp. 1-11.

* cited by examiner

SYSTEMS AND METHODS FOR INDICATING ABERRANT BEHAVIOR DETECTED BY AN IMPLANTED MEDICAL DEVICE

CROSS REFERENCE TO RELATED APPLICATIONS

The present application is a continuation-in-part of U.S. patent application Ser. No. 10/793,177 filed on Mar. 4, 2004 now abandoned. The entirety of the aforementioned application is incorporated herein by reference for all purposes.

BACKGROUND OF THE INVENTION

The present invention is related to implantable medical devices, and in particular to a cardiac arrest and/or sleep apnea monitoring devices capable of detecting aberrant behavior and/or implementing corrective action in relation to a detected aberrant behavior.

A large number of people suffer from obesity and/or heart disease. In these people, it is common to find heightened respiratory discomfort and shortness of breath during periods of sleep. In addition, these people often experience breathing characterized by rhythmic waxing and waning of the depth of respiration with regularly recurring periods of apnea, clinically described as Cheyne-stokes breathing.

In general, there are two kinds of sleep related apnea that are associated with heart disease. First, central sleep apnea is the most common type found and is probably caused by heart failure. This type of apnea may be developed after a heart attack and is usually a contributing factor to heart failure. During central sleep apnea, patients stop breathing and begin to suffocate causing them to wake-up. The awakening jolts their heart muscles into action when they should be resting and thus the jolting action puts stress on the heart.

The other type of sleep related apnea is obstructive sleep apnea and may contribute to heart failure. Obstructive sleep apnea is commonly found in people with oversized necks. Such people are typically overweight and suffer from snoring. Muscle tone keeps the throat open during the day, but at night the weight of the oversized neck narrows the airway. As a result, the tongue falls back closing the airway. The person struggles to breath against the collapsed throat as if choking. This breathing effort can put an additional strain on the heart.

Excessive pressure on the heart can be created during periods of apnea. These excessive pressures can be particularly problematic for patients already suffering from heart disease. In some cases, these excessive pressu3res can cause heart attack and/or death. Accordingly, for at least the aforementioned reasons, there exists a need in the art for advanced respiratory and/or heart function detection, and/or systems and methods for intervention where aberrant behavior is detected.

BRIEF SUMMARY OF THE INVENTION

The present invention provides various systems and methods for intervening where aberrant heart, respiratory, and/or other dysfunction is detected. For example, some embodiments of the present invention provide a monitor capable of detecting the occurrence of sleep apnea, and for audibly alerting the patient (or a spouse or caregiver associated with the patient) in which the sleep apnea is detected. In some cases, a pacemaker or some other medical device detects an abnormality indicative of the sleep apnea. An information signal indicating the detected aberrant condition is transmitted from the pacemaker to a bedside monitor. Based on the received information signal, the bedside monitor can sound an audible alarm to awake the patient. Further, in some cases, an electrocardiogram (EGM) and/or other physical signals sensed by the pacemaker can be transmitted from the bedside monitor to a remote monitor. Information can be retrieved from the remote monitor by a clinician and used in real time, or at a later time to diagnose and/or treat the patient. Further, in some cases, the remote monitor can dispatch emergency medical personnel to the location indicated by the bedside monitor. Because of the patient information provided to the remote monitor, the emergency medical personnel can arrive at the patient's location prepared to intervene.

Various embodiments of the present invention provide systems for detecting aberrant behavior of a living being. Examples of such aberrant behavior includes, but is not limited to, a lack of heart functionality, a low heart rate, a high heart rate, a sleep apnea, an atrial fibrillation, a ventricular fibrillation, a shallow breathing, a lack of breathing, and/or the like. Such systems include, a receiver capable of receiving an information signal from a deployed, implantable medical device. The information signal is received via a wireless transmission from the medical device, and thus, the receiver is disposed within a telemetry range associated with the deployed, implantable medical device. In some cases, this telemetry ranges is very limited, and thus the receiver includes a sensor, such as, for example, a thin, small adhesive backed receiver to be applied to the skin of a patient in which the implantable medical device is deployed. In other cases, the telemetry range is significant allowing for reception of the information signal at a distance of several feet or more from the deployed, implantable medical device.

The systems further include a processor that is capable of associating a time stamp with the information signal received from the deployed, implantable medical device. In some cases, additional information can also be associated with the information signal such as, for example, a physical location of the processor. This information can be transmitted along with the time stamp and diagnostic information from the information signal to a remote monitor via a communication system. The remote monitor can use the transmitted information for immediate or later diagnosis and treatment, and/or for dispatching emergency medical assistance.

The systems also include a therapy delivery system that is operable to initiate a therapy based at least in part on the information signal from the deployed, implantable medical device. In one particular case, the information signal from the deployed, implantable medical device indicates an occurrence of sleep apnea, and the therapy delivery system includes a speaker that is operable to emit an audible noise upon the occurrence of sleep apnea. In another case, the information signal from the deployed, implantable medical device indicates an occurrence of a particular aberrant, and the therapy delivery system includes a programmer operable to transfer programming parameters to the implantable medical device in response to the particular aberrant behavior.

In various instances, the systems further include a diagnostic system that is operable to determine an aberrant behavior based at least in part on the information signal from the deployed, implantable medical device. In other instances, the deployed, implantable medical device includes a diagnostic system operable to identify an aberrant behavior, and the information signal from the deployed, implantable medical device indicates the aberrant behavior. In yet other instances, both the deployed, implantable medical device and the system include diagnostic systems that can each perform all or a portion of diagnosing aberrant behavior.

Other embodiments of the present invention provide systems for indicating an irregular physical condition. Such systems include a local monitor and a programmer disposed at a first distance to a deployed, implantable medical device. As an example, where the deployed, implantable medical device utilizes inductive telemetry, a receiver could be a standalone telemetry/alarm which is applied to the skin of the living being near the deployed, implantable medical device. Alternatively, where a stronger transmitter allows for an increased telemetry range, the receiver can be included in a monitor placed some distance from the living being. The local monitor includes a diagnostic system and an alert system. In addition, the systems include a remote monitor disposed at a second distance to the deployed, implantable medical device. The remote monitor is communicably coupled to the local monitor.

In some cases, the programmer is communicably coupled to the local monitor and is operable to initiate a therapy based at least in part on an output from the diagnostic system operating on information received from the deployed, implantable medical device. In particular cases, the diagnostic system is operable to detect sleep apnea, and when sleep apnea is detected, a speaker associated with the alert system sounds an audible alarm. The speaker can be located remote or local to the patient in which the implantable device is employed. Thus, for example, the speaker can sound an audible alarm local to the patient such that the patient is woken, or the speaker can be in a caregiver's room next to the patient's room. Sounding the audible alarm awakens the caregiver who in turn can alert the patient.

In various cases, the system further includes a communication device that is operable to provide communication between the local monitor and the remote monitor. This communication device can be one of a number of device types including, but not limited to, an analog modem, or a digital based communication device.

Yet other embodiments of the present invention provide systems for mitigating an irregular physical condition. The systems include a local monitor disposed within a telemetry range of a deployed, implantable medical device. The local monitor includes a processor that is communicably coupled to a computer readable medium. The computer readable medium includes instructions executable by the processor to receive an information signal from the deployed, implantable medical device; associate a time stamp with the information signal from the deployed, implantable medical device; initiate a therapy based at least in part on the information signal from the deployed, implantable medical device; and communicate a message to a remote monitor based at least in part on the information signal from the deployed, implantable medical device and the time stamp.

Yet further embodiments of the present invention provide methods for mitigating an irregular physical condition. The methods include receiving an information signal from a deployed, implantable medical device at a local monitor. The information signal is stored and associated with a time stamp. Based at least in part on the information signal from the deployed, implantable medical device, a therapy is initiated. Further, the methods include communicating a message based at least in part on the information signal and the time stamp to a remote monitor disposed beyond the telemetry range of the deployed, implantable medical device. In some cases, communication between the local monitor and the remote monitor is performed over a wired and/or wireless transmission medium including, but not limited to, a cellular telephone link, the Internet, a virtual private network, a public switched telephone network, and/or combinations thereof.

In some cases, the therapy includes sounding an external alarm designed to awaken a sleeping patient or to alert a caregiver, while in other cases, the therapy involves modifying the functionality of the deployed, implanted medical device. Modifying the functionality of the deployed, implantable medical device can include, but is not limited to, delivering a shock from an implanted pacemaker and/or speeding heart rate parameters controlled by the pacemaker.

This summary provides only a general outline of some embodiments of the present invention. Many other objects, features, advantages and other embodiments of the present invention will become more fully apparent from the following detailed description, the appended claims and the accompanying drawings.

BRIEF DESCRIPTION OF THE DRAWINGS

A further understanding of the various embodiments of the present invention may be realized by reference to the figures which are described in remaining portions of the specification. In the figures, like reference numerals are used throughout several to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

The present invention provides various systems and methods for intervening where aberrant behavior of a living being is detected. The aberrant behavior can include, but is not limited to, a malfunction of the heart or shallow breathing. As one particular example, some embodiments of the present invention provide a monitor capable of detecting the occurrence of sleep apnea, and for audibly alerting the patient in which the sleep apnea is detected or a spouse of the patient. In some cases, a pacemaker or some other medical device detects an abnormality indicative of the sleep apnea, and an information signal indicating the detected condition is transmitted from the pacemaker to a bedside monitor. In addition, the information can be communicated from the local monitor to a remote monitor. The remote monitor can be accessed by a clinician and used in real time, or at a later time to diagnose and/or treat the patient. Further, in some cases, the remote monitor can dispatch emergency medical personnel to the location indicated by the bedside monitor. Because of the patient information provided to the remote monitor, the emergency medical personnel can arrive at the patient's location prepared to intervene.

As used herein, the terms "aberrant behavior" and "irregular physical condition" are is used in the broadest sense, and can include any function of a living being or devices implanted in the living being that is outside an established range. Thus, as just some examples, aberrant behavior can include a sleep apnea, an atrial fibrillation, a ventricular fibrillation, a shallow breathing, a lack of breathing, a lack of heart functionality, a low heart rate, a high heart rate, and/or a malfunction of a deployed, implantable medical device. Also, as used herein the term "deployed, implantable medical device" is used in its broadest sense and can be any device deployed either internal to or integrally attached to a living being. These devices are typically capable of monitoring, controlling, and/or intervening in the functionality of the living being. As just one example, a deployed, implantable medical device can be a pacemaker capable of delivering stimuli to a heart, and monitoring various life functions associated with the living being. Such deployed, implantable medical devices can include one or more of a plethora of sensors known in the art that are able to detect patient conditions including, but not limited to, an evoked response sensor to detect ventricular or atrial fibrillation, a minute ventilation sensor to detect breathing or a lack thereof, sense amplifiers to detect a beating heart in the atrium and ventricle, and/or the like. As used herein, a living being can be a human, or another animal.

Figure 1:
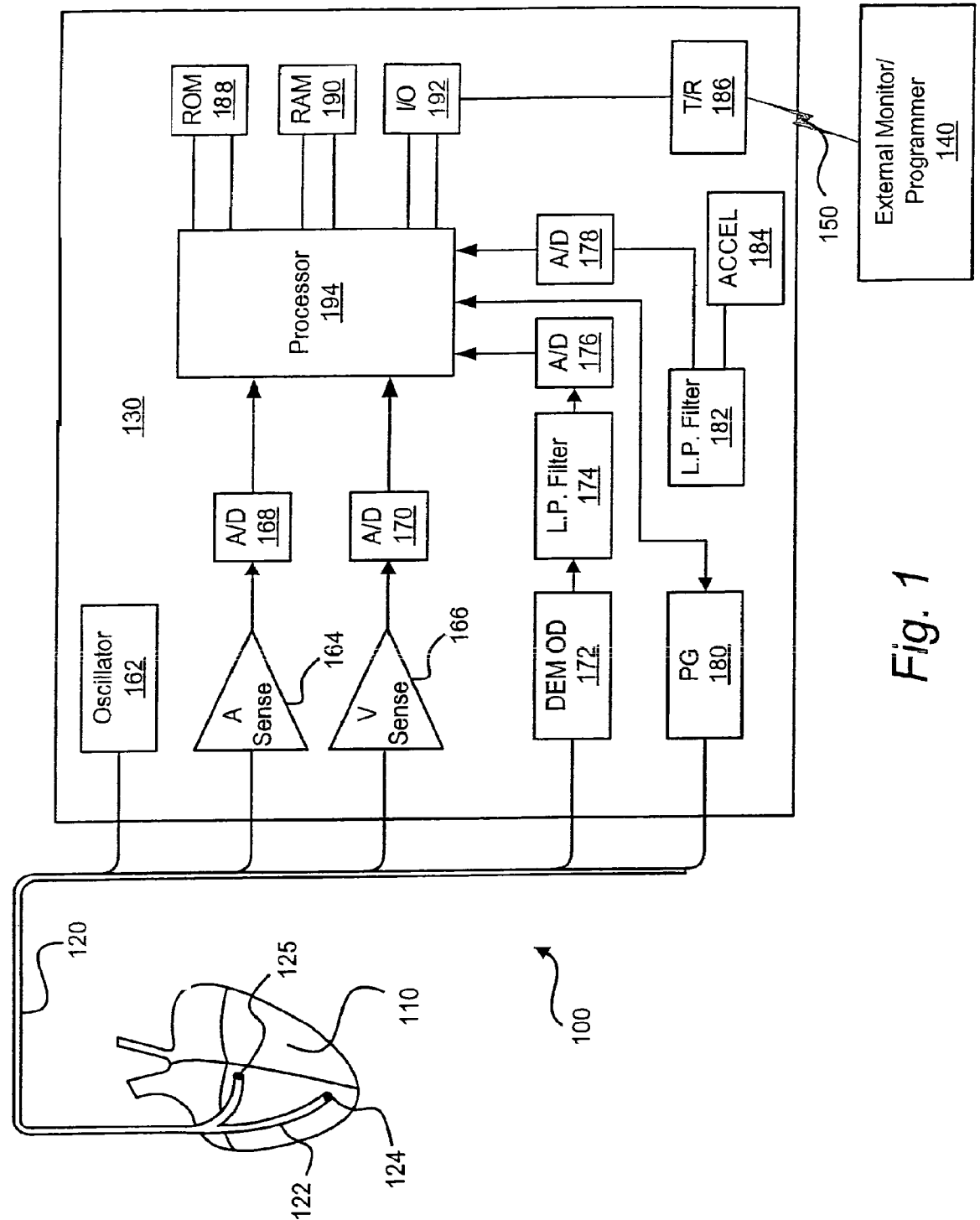
FIG. 1 depicts an exemplary implantable medical device that can be used in relation to embodiments of the present invention.

Turning to FIG. 1, an exemplary implantable medical device 100 is depicted in relation to a human heart 110. As illustrated, implantable medical device 100 is a cardiac rhythm device, but as previously stated, can be any type of implantable medical device as that term is understood in its broadest sense. The illustrated device is more fully described in U.S. Pat. No. 5,974,340 which is incorporated herein in its entirety for all purposes. In this case, implantable medical device 100 is operatively connected to a patient's heart 110 by electrical conductors embodied in a pacing lead 120. A housing 130 of the implantable medical is implanted in a surgically made pocket, typically in either the left or right pectoral region of the patient. Implantable medical device 100 includes microprocessor-base controller 194 that is programmed to operate in a plurality of modes, well known to those skilled in the art. Microprocessor based controller 194 has a RAM (random access memory) 190 and a ROM (read only memory) 188 for storing programs and data. Microprocessor based controller 194 controls the delivery of cardiac stimulation pulses by a pulse generator 180 to simulating electrodes 122, 124 and 125 on pacing lead 120. Electrode 124 is connected to a ventricular sense amplifier 166 and electrode 125 is connected to the atrial sense amplifier 164. The electrodes 122, 124, 125 are arranged to sense the atrial and ventricle depolarization events depending upon the programmed mode of the cardiac rhythm management device being utilized. The signal representing the sensed activity is fed to an analog-to-digital converter 168 and 170, respectively, and then the digitized signal is fed to the input of microprocessor-based controller 194 for evaluation and for determining cardiac stimulation.

As illustrated, an accelerometer 184 is positioned within housing 130 of the cardiac rhythm management device and coupled to microprocessor-based controller 194 via an analog to digital converter 178. By positioning accelerometer 184 in casing 130, accelerometer 184 generates a global signal associated with the various atrial and ventricular events. Where implantable medical device 100 is to be used to measure intracardiac impedance, an oscillator 162 is incorporated within case 130 for applying a high frequency carrier between electrodes 122 and 124 in the right ventricle or between metal case 130 and electrode 124.

The analog signal output of accelerometer 184 indicates events associated with the heart sounds, compressions, cardiac wall accelerations and decelerations caused by cardiac events along with motion artifacts and respiratory events. The signal is passed through a low pass filter 182. The resultant wave form can be associated with respiration or minute volume. The accelerometer signal is transmitted to an analog to digital converter 178 where it is digitized before being transmitted to the microprocessor-based controller 194. At microprocessor-based controller 194, the digitized signal is processed and analyzed.

Respiration may also be monitored from the intracardiac impedance measurements. As well known in the art, oscillator 162 is used to provide a relatively high frequency, low amplitude alternating current for impedance measurement. A carrier frequency typically between 1 kHz and 100 kHz may be used. The respiratory or pulmonary and cardiac signals modulate the carrier and are readily separated from the high frequency carrier by a demodulator 172. The intracardiac impedance measurements are generally low-pass filtered with a filter 174 to isolate the ventilation activity where amplitude is related to tidal volume. More particularly, this signal may be low-pass filtered at about a 2 Hz cut off frequency to isolate the ventilation activity component.

Programming parameters for operating implanted medical device 100 can be received from a local external monitor/programmer 140 via a wireless communication link 150. Further, an information signal from implantable medical device 100 can be provided to local external monitor/programmer 140 via communication link 150. In particular, information (e.g., a number of parameters) can be organized by microprocessor-based controller 194, passed to an input/output port 192, and then transmitted by a transceiver 186 to local external monitor/programmer 140. In the reverse, programming parameters can be passed from local external monitor/programmer 140 to transceiver 150 via communication link 150. These parameters can then be passed via input/output port 192 and to microprocessor-based controller 194. These parameters can be used to modify the operation of implantable medical device 100.

As set forth in greater detail in U.S. Pat. No. 5,974,340, various implantable medical devices including, but not limited to, the device described in relation to FIG. 1 measure activity and respiratory signals for the purposes of rate adaptive pacing. Respiration can be determined by minute ventilation which is the product of respiratory rate and tidal volume. Minute ventilation is estimated by frequent measurements of trans-thoracic impedance between an intracardiac lead and the pulse generator case using a bipolar system. Further details regarding trans-thoracic impedance can be found in U.S. Pat. No. 6,684,101. The entirety of the aforementioned patent is incorporated herein by reference for all purposes. A low energy pulse of known current amplitude, well below the threshold of stimulation, is delivered from the ring electrode of a standard bipolar pacing lead. The resultant voltage between the tip electrode and the pulse generator case is measured and the impedance is calculated. By measuring the frequency of respiration, related fluctuations in impedance (correlated with respiratory rate) and the amplitude of those excursions (correlated with tidal volume) minute ventilation can be estimated. The respiratory information derived from the impedance waveform can be used as a physiological functional parameter for determining optimum pacing rate in a rate responsive pacer or can be used to monitor respiratory activity.

The trans-thoracic impedance signal is a complex parameter influenced by several factors. However, the trans-thoracic impedance is most closely related to the volume and resistivity of the blood in the heart and the systemic venous system. The impedance signal fluctuates in response to both respiration and cardiac motion (ventricular ejection). This information can be quantified and passed from deployed, implantable medical device 100 to local external monitor/programmer 140 via communication link 150.

Figure 2:
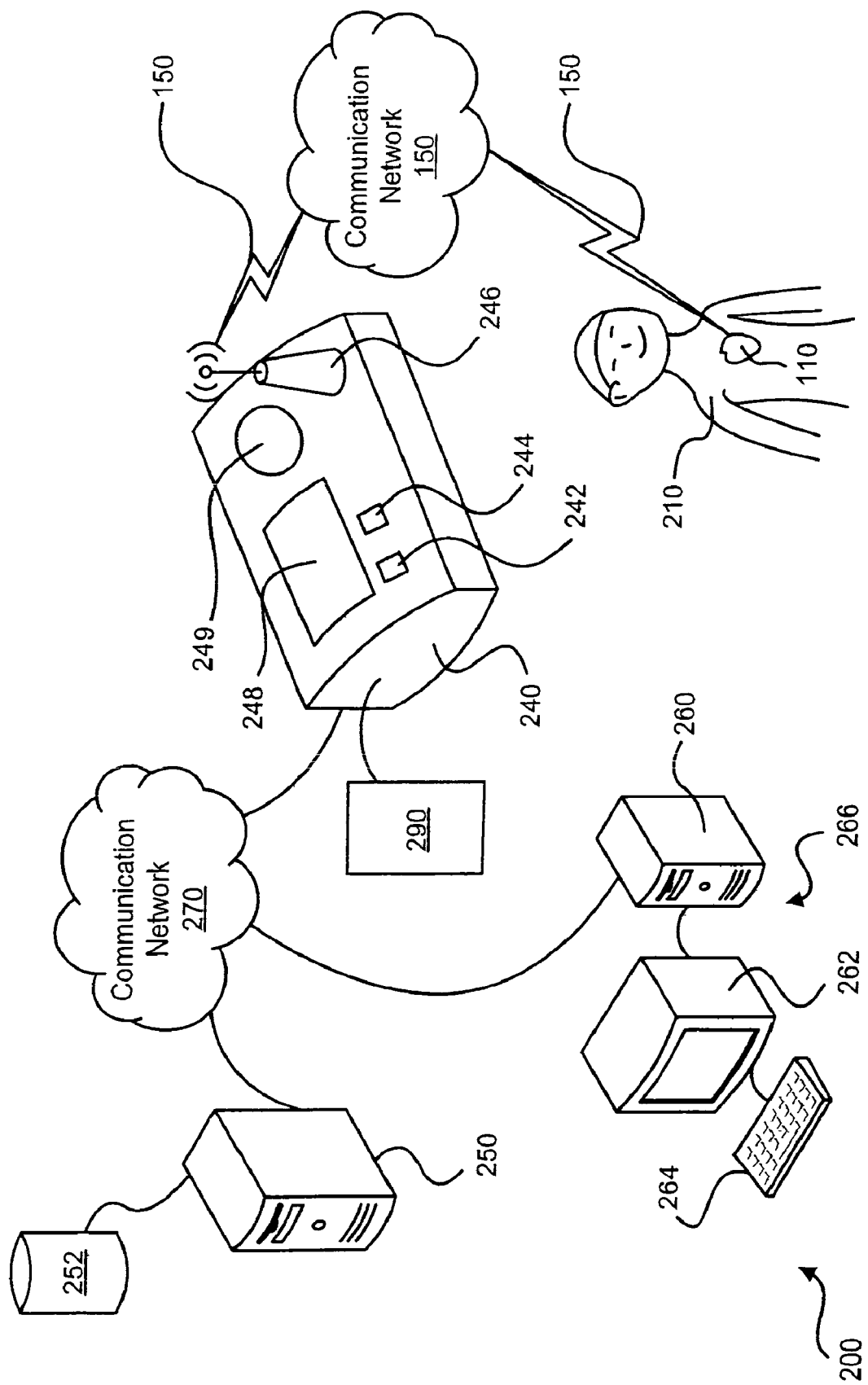
FIG. 2 illustrates a system in accordance with various embodiments of the present invention.

Turning to FIG. 2, a system 200 in accordance with various embodiments of the present invention is illustrated. System 200 includes local external monitor/programmer 240 communicably coupled to a remote monitor 250 via a communication network 270. Local external monitor/programmer 240 includes an antenna 246 that provides for communication with a deployed, implantable medical device 110 disposed within a living being 210. Local external monitor/programmer 240 further includes a speaker 249 capable of emitting an audible signal, and a display 248 capable of providing one or more messages related the operation of deployed, implantable medical device 110. Further, local external monitor/programmer 240 includes one or more input mechanisms 242, 244 used to control operation of the device.

Communication network 270 can be any communication network including, but not limited to, the Internet, a virtual private network, a local area network, a pager network, a cellular telephone network, a public switched telephone network, a direct wired connection, combinations of the aforementioned, and/or the like. Remote monitor 250 is communicably coupled to a database 252. As used herein, the term "communicably coupled" is to be interpreted in its broadest sense, and indicates any coupling whereby information can be passed from a source to a destination. Thus, two devices can be communicably coupled where they communicate via a wire, or where they communicate wirelessly. System 200 also includes a remote access station 266 comprised of a computer 260, monitor 262 and input device 264. Remote access station 266 is communicably coupled to remote monitor 250 and/or local external monitor/programmer 140, and can access and utilize information maintained on database 252.

In operation, an information signal is passed from deployed, implantable medical device 110 via communication link 150 to local external monitor/programmer. In some cases, the information signal indicates one or more aberrant behaviors detected in relation to living being 210 and/or deployed, implantable medical device 110. Upon receiving this information signal, local external monitor/programmer 140 can perform one of a number of functions. Local external monitor/programmer 140 can associate a time stamp with the received information signal and store both the time stamp and the received information signal. In some embodiments, the deployed, implantable medical device associates a time stamp with the episode information. In various cases, the information signal passed from the deployed, implantable medical device includes one or more event counters and stored electrograms. Such event counters can include an indication of the number of incidents of sleep apnea detected, and/or the like.

In addition, local external monitor/programmer 140 can apply diagnostic tests to the received information and select one or more therapies to be provided. For example, where sleep apnea is indicated, an audible alarm can be sounded via speaker 249 in an attempt to awaken living being 210. Alternatively, or in addition, an audible alarm can be sounded via a speaker 290 located remote from living being 210. The remote location can be, for example, near a caregiver who in turn can attempt to awaken living being 210 and/or provide additional care. For example, the caregiver could apply external defibrillation where an un-converted tachycardia is detected, or could apply a some shock event when living being 210 is unconscious or vulnerable.

Further, diagnostic tests run by one or both of local external monitor/programmer 140 and deployed, implantable medical device 110 may indicate initiation of a therapy using deployed, implantable medical device 110 to deliver that therapy. In such a case, deployed, implantable medical device 110 may initiate the therapy on its own.

Alternatively, local external monitor/programmer 140 can upload operational parameters via communication link 150 to deployed, implantable medical device 110 directed at initiating the therapy. In turn, deployed, implantable medical device can implement the received operational parameters directed at alleviating or curing the detected aberrant behavior. Thus, for example, where sleep apnea is detected, parameters to speed the heart rate may be uploaded to deployed, implantable medical device. Alternatively, where some form of arrhythmia is detected, parameters causing a shock to be delivered to the heart may be uploaded to deployed, implantable medical device. Based on the disclosure provided herein, one of ordinary skill in the art will recognize a number of possible therapies that can be implemented in relation to living being 210 and/or deployed, implantable medical device 110.

In addition, local external monitor/programmer 140 can upload incident information to remote monitor 250 via communication network 270. This incident information can include the information signal received from deployed, implantable medical device 110, and a time stamp applied by local external monitor/programmer 140. In addition, any diagnostics performed by local external monitor/programmer 140, parameter changes performed by local external monitor/programmer 140, and/or the physical location of local external monitor/programmer 140 can be uploaded to remote monitor 250.

This incident information can then be accessed via one or more remote access stations 266. Thus, for example, where the patient is suffering from sleep apnea, the patient's physician may use a remote access station 266 to evaluate the progress of the patient. This can be done in real time, or later during, for example, the patient's next scheduled appointment with the physician. Where monitoring is ongoing in real time, the physician may enter programming commands that cause local external monitor/programmer 140 to implement a particular therapy specified by the physician. As previously discussed, the therapy can be external in the form of an audible alarm and/or internal in the form of a modification of the parameters of deployed, implantable medical device 110.

In one particular case, remote access station 266 is located in a physician's office, while in other cases, remote access station 266 is located in an emergency dispatch office or in an ambulance. Thus, in some cases, remote access station 266 can be used to alert emergency medical personnel about an ongoing aberration, and dispatch the personnel to the patient's location based on the location information provided by local external monitor/programmer 140. Based on the disclosure provided herein, one of ordinary skill in the art will recognize a number of other locations that would be benefited by a remote access station.

Figure 3A:
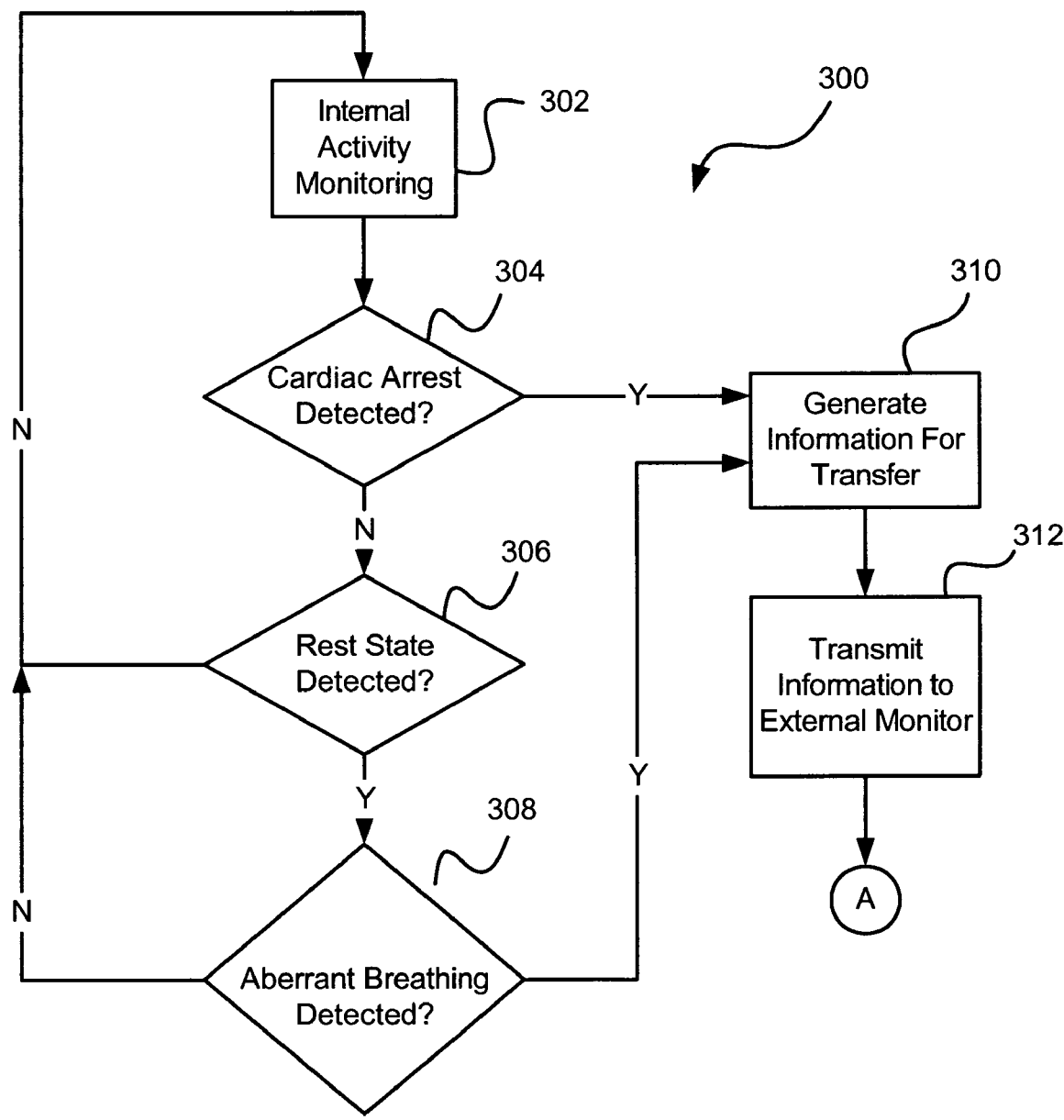
FIG. 3 are flow diagrams that illustrate system operation in accordance with some embodiments of the present invention.

Turning to FIG. 3, a flow diagram 300 describing a method in accordance with various embodiments of the present invention is discussed. Following flow diagram 300, internal activity of a living being is monitored via a deployed, implantable medical device (block 302). This monitoring includes detection of one or more aberrant behaviors. Thus, for example it is determined whether a cardiac arrest is detected (block 304). Where a cardiac arrest is not detected (block 304), it is determined if the patient is in a restive state (block 306), where the patient may be exposed to the occurrence of sleep apnea. Where the patient is in a restive state, it is determined if the patient's respiration indicates the onset of sleep apnea (block 308). Where either the patient is not resting (block 306) or that respiration is normal (block 308), the monitoring is continued (block 302). It will be appreciated that the aberrant behaviors used in flow diagram 300 (blocks 304, 308) are merely exemplary and that a myriad of other behaviors can be detected in addition to or in place of those described.

Where a cardiac arrest is detected (block 304) or where abnormal respiration is detected (block 308), a number of parameters monitored by deployed, implantable medical device 110 are prepared for transfer (block 310). In some cases, deployed, implantable medical device 110 can monitor several hundred or more parameters. With the information prepared for transfer (block 310), it is transmitted to local external monitor/programmer 140 (block 312). In one particular case, the information signal transmitted is a binary encoded signal.

Figure 3B:
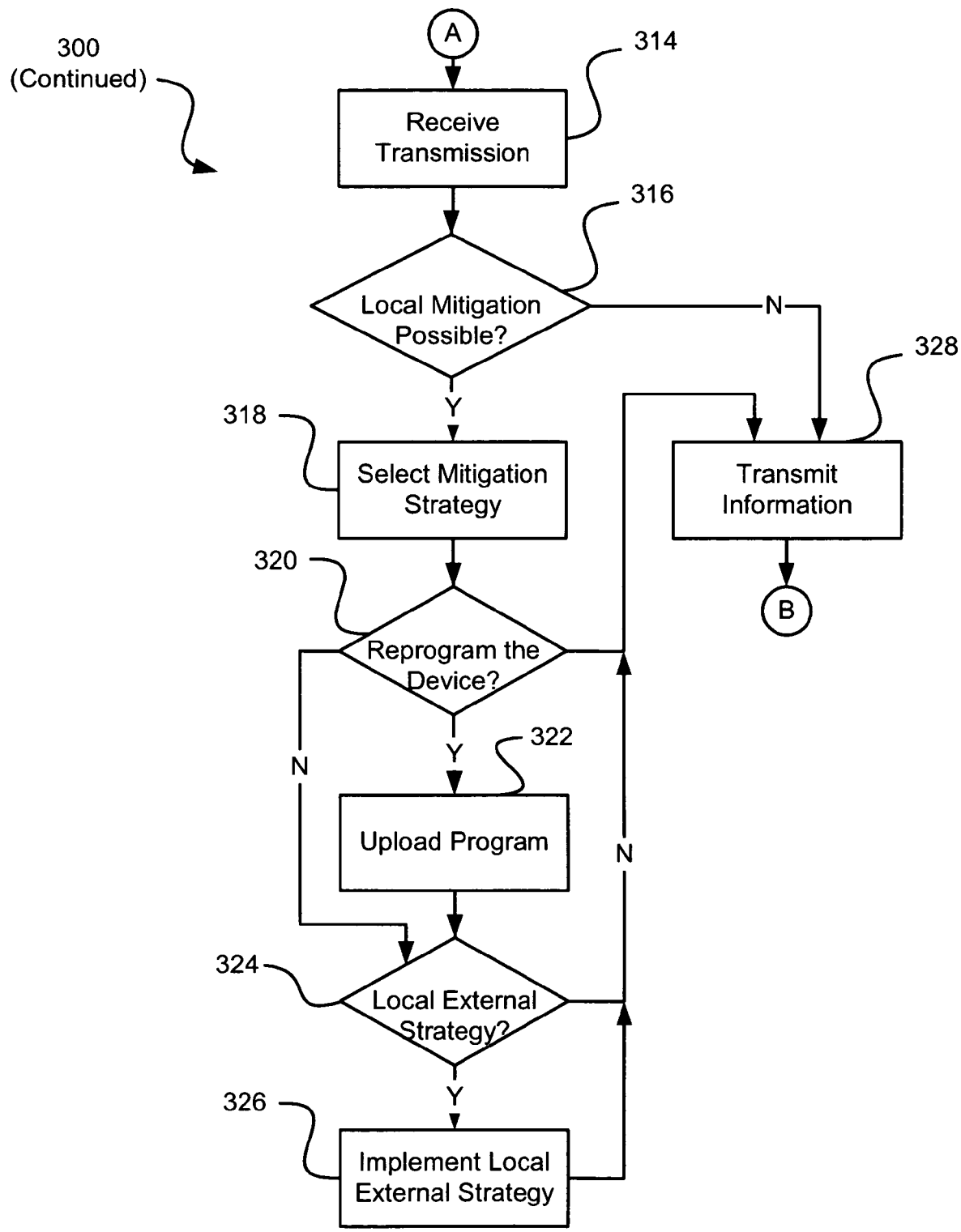

Turning to FIG. 3b, the transmitted information is received by local external monitor/programmer 140 (block 314). It is determined if the indicated aberrant behavior can be mitigated locally (block 316). If local mitigation is possible (block 316), a mitigation strategy or therapy is selected based on a diagnostic system implemented as part of local external monitor/programmer 140 (block 318). It is determined if the selected therapy requires programming of deployed, implantable medical device 110 (block 320). Where programming is called for (block 320), operational parameters associated with the therapy are selected and uploaded from local external monitor/programmer 140 to deployed, implantable medical device 110 (block 322). Further, it is determined if a local external strategy or therapy is called for (block 324). Where such an external therapy is called for (block 324), the external therapy is implemented (block 326).

Figure 3C:
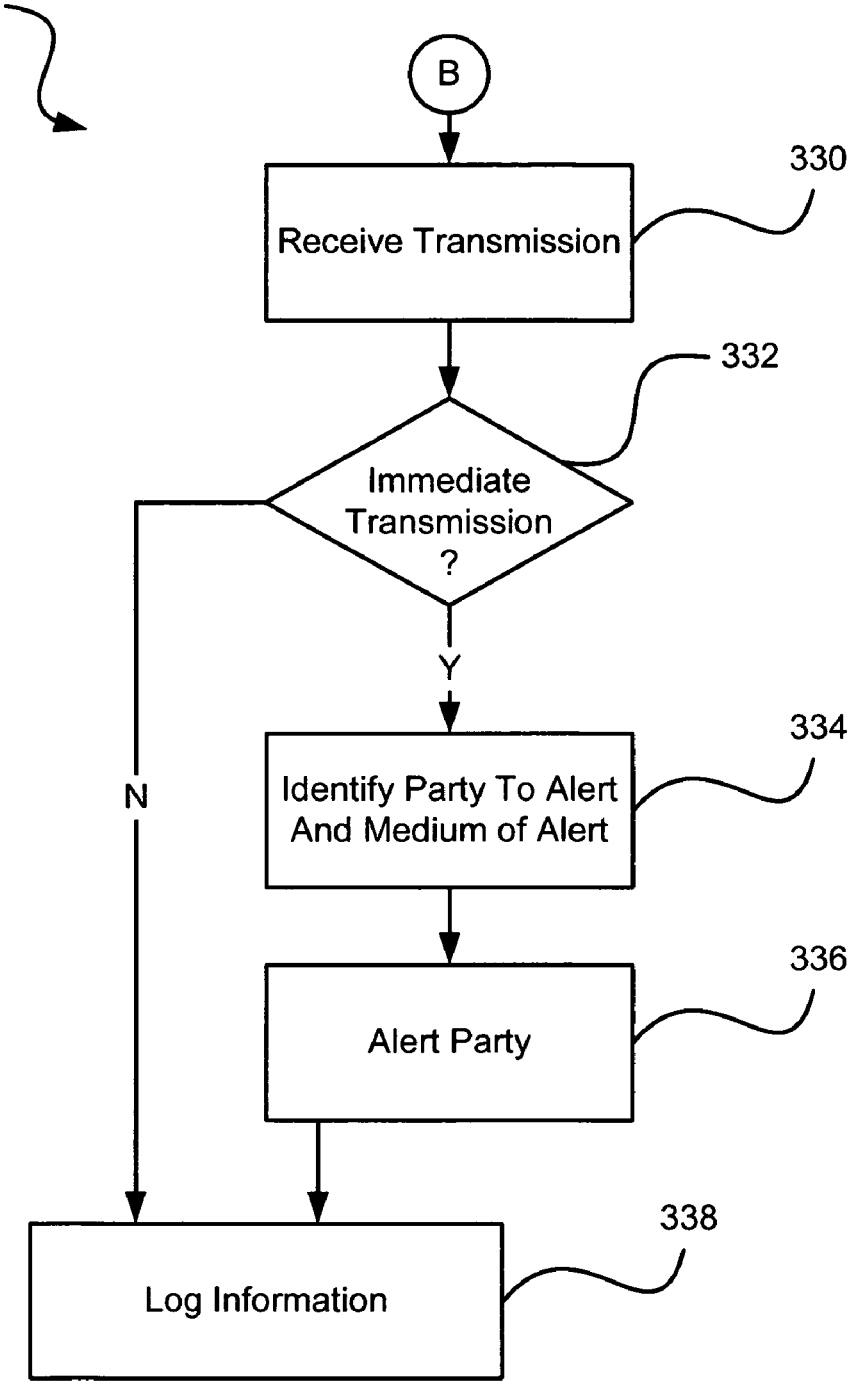

In addition, the information from local external monitor/programmer 140 is transmitted to remote monitor 250 (block 328). Turning to FIG. 3c, remote monitor 250 receives the information transmitted from local external monitor/programmer 140 (block 330). It is determined if the information transmitted requires immediate attention, or if it can merely be recorded for later consideration (block 332). Where the information indicates the need for immediate attention (block 332), a party to be alerted is identified (block 334) and the party is alerted (block 336). This can include, but is not limited to, emergency medical personnel. Thus, for example, a message including the information from local external programmer 140 can be transferred to an ambulance station, and the ambulance can be dispatched to the location of the local external programmer 140. Alternatively, or in addition, the information can be transferred to an emergency room that can thus be prepared to receive the patient transported in the ambulance. Based on the disclosure provided herein, one of ordinary skill in the art will recognize a number of other parties that can be alerted in accordance with various embodiments of the present invention.

In addition, the information from local external programmer 140 is stored to a database communicably coupled to remote monitor 250 (block 338). This information can be accessed at a later time by, for example, a physician or other medical personnel and used to treat and/or diagnose the patient.

Figure 4:
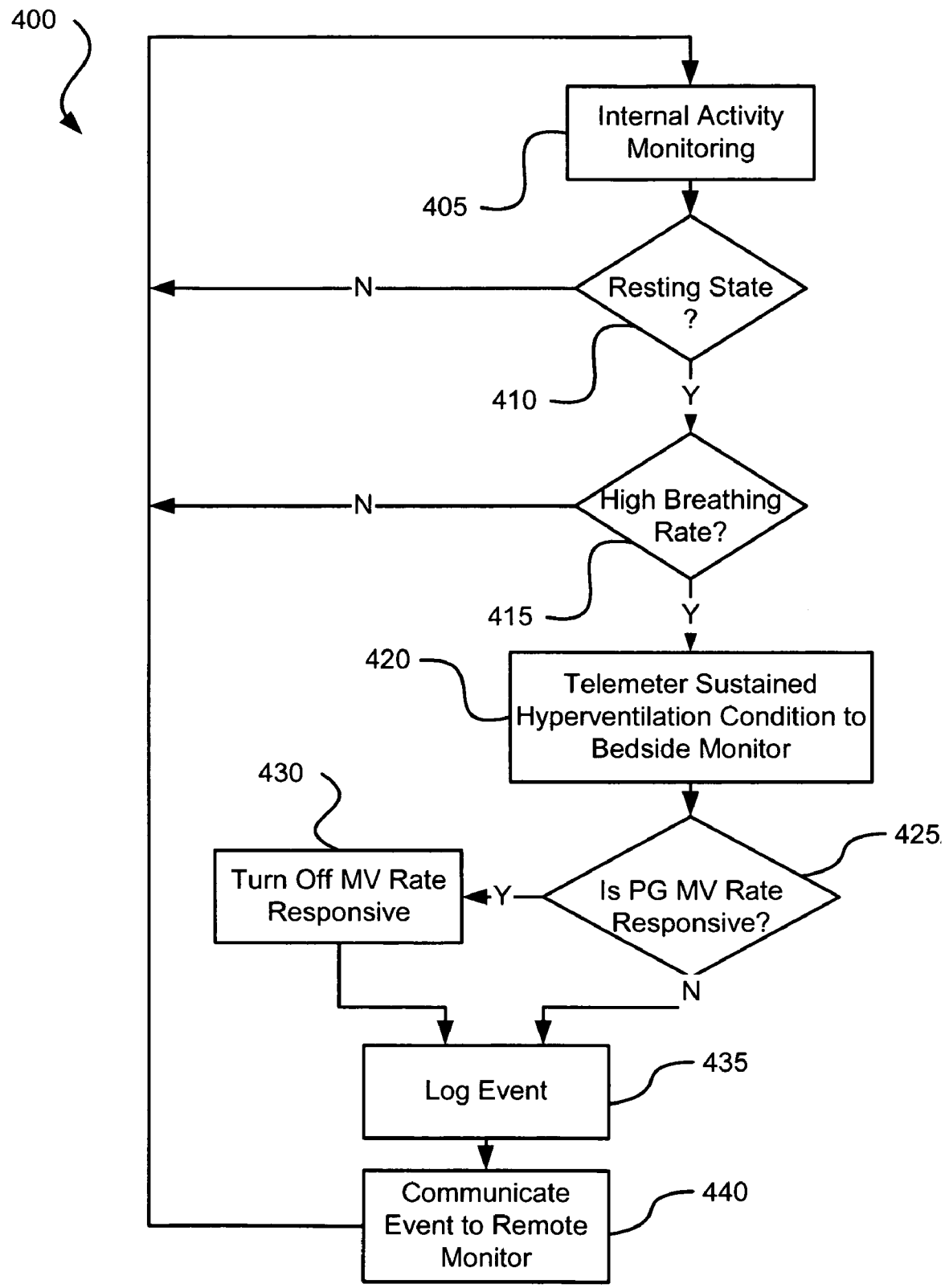
FIG. 4 is a flow diagram illustrating a method in accordance with various embodiments of the present invention for detecting and intervening in sustained hyperventilation.

Turning to FIG. 4, a flow diagram 400 illustrates a method in accordance with various embodiments of the present invention for detecting and intervening in sustained hyperventilation. Following flow diagram 400, activity monitoring is performed by a pacemaker (PG) (block 405). A sustained hyperventilation condition is indicated when a resting state of the patient under monitor (block 410) along with a high breathing rate (block 415) are detected. Such a high breathing rate can be, for example, detected using minute ventilation transthorasic impedance monitoring over time. Where it is determined that the patient is involved in some level of physical activity that justifies a higher breathing rate, then the high breathing rate is considered normal and no notification is provided. Alternatively, where it is determined that the patient is in a resting or sedentary state and a sustained high breathing rate is observed, sustained hyperventilation is indicated (blocks 410, 415), and the detected condition is communicated by the PG to the bedside monitor (block 420). The bedside monitor queries the PG to determine if the PG is modifying the atrial or ventricular pacing rate based on the breathing rate (i.e., the PG MV rate responsive)(block 425). If it is determined that the PG is responsive to the breathing rate (block 425), the bedside monitor programs the PG with updated parameters (block 430) that cause the PG to discontinue pacing modification with respect to the breathing rate. The pacing rate would then typically drop to a more appropriate rate that is not influenced by the high breathing rate. At this point, the event is logged (block 435) and communicated to a remote monitor (block 440). Alternatively, where the PG is not breathing rate responsive (block 425) the event is logged (block 435) and communicated to a remote monitor (block 440).

Figure 5:
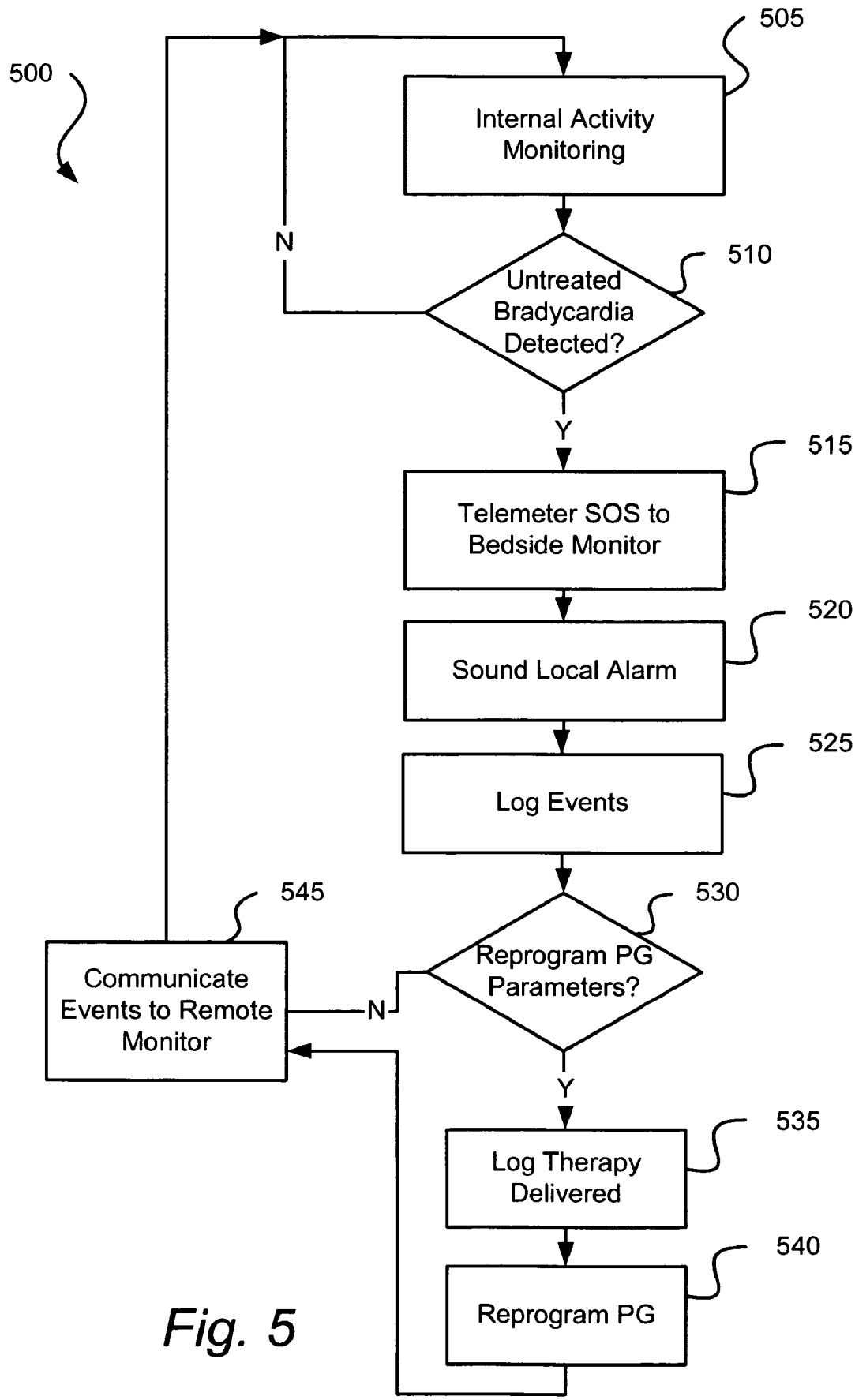
FIG. 5 is a flow diagram depicting a method in accordance with some embodiments of the present invention for detecting and intervening in bradycardia.

Turning to FIG. 5, a flow diagram 500 depicts a method in accordance with some embodiments of the present invention for detecting and intervening in untreated bradycardia. Untreated bradycardia occurs when a patient's intrinsic heart rate is allowed to drop to less than forty to fifty beats per minute. Such a low heart rate can result in fainting or other indications of stress. It is untreated where the PG does not automatically mitigate this occurrence. Following flow diagram 500, activity monitoring is performed by a PG (block 505). Where the PG detects an untreated bradycardia (block 510), an alarm or SOS signal is communicated to a bedside monitor indicating the detected low pacing rate (block 515). The bedside monitor sounds a local alarm (block 520), and the condition as well as events surrounding the condition are logged (block 525). In addition, the bedside monitor queries the PG to determine if the PG can be reprogrammed to address the detected condition (block 530). Thus, for example, it can be determined if a rate drop feature in the PG is enabled which is allowing the detected condition to occur. As other examples, it can be determined if the lower rate limit on the PG device is simply programmed too low, or if there are other rate modifying features enabled that are allowing the rate to drop too low. If it is determined that the PG can be reprogrammed to alleviate the detected condition (block 530), the proposed therapy (e.g., reprogramming) is logged (block 535) and a program implementing the therapy in the PG is loaded to the PG (block 540). Thus, for example, if it is determined that a rate drop feature in the PG is enabled and potentially causing the condition, the feature can be disabled. Alternatively, or in addition, where it is determined that the minimum rate is programmed too low, it can be adjusted to a higher rate. Where neither of the aforementioned situations exist, the monitor can further evaluate if there are other pacing rate modifiers that are causing the detected condition. If so, these modifiers can be disabled. The detected condition and events detected in relation to the condition are communicated to the remote monitor (as well as any reprogramming of the PG) (block 545).

Figure 6:
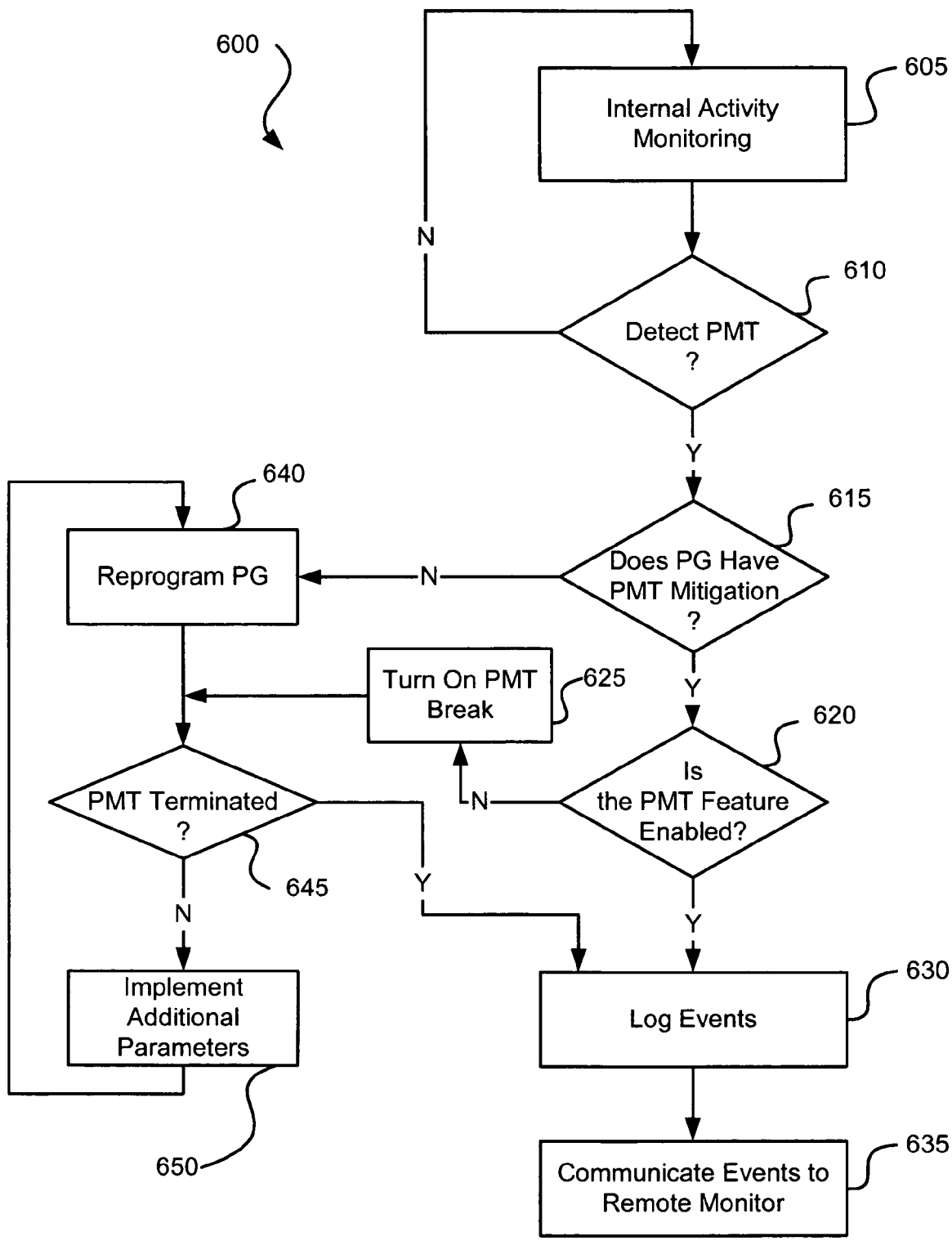
FIG. 6 is a flow diagram illustrating a method in accordance with some embodiments of the present invention for detecting and intervening in pacing minimum threshold.

Turning to FIG. 6, a flow diagram 600 depicts a method in accordance with some embodiments of the present invention for detecting and intervening pacemaker mediated tachycardia (PMT). Following flow diagram 600, activity monitoring is performed by a PG (block 605). Where the PG detects PMT (block 610), it is determined if the PG includes PMT mitigation capability (block 615). Where such capability is found (block 615), it is determined if the capability is enabled and properly mitigating the PMT (block 620). Where the capability is not enabled or not properly mitigating the PMT (block 625), the PG is programmed to enable the capability (block 625). Alternatively, where the mitigation capability is enabled and properly mitigating PMT (block 620), the events surrounding the detection of the PMT as well as the mitigation efforts are logged (block 630) and communicated to a remote monitor (block 635).

Alternatively, where it is determined that the PG does not include PMT mitigation capability (block 615), the bedside monitor determines one or more parameters to be programmed into the PG allowing for mitigation of the detected condition, and the parameters are programmed to the PG (block 640). It is determined whether the detected PMT has been mitigated (block 645), and if it has not, additional PG parameters are selected (block 650) and programmed into the PG (block 640). This process can continue until mitigation of the PMT is complete or until some defined point. Where it is determined that the PMT has been mitigated (block 645), the events surrounding the detection of the PMT as well as the mitigation efforts are logged (block 630) and communicated to a remote monitor (block 635).

Figure 7:
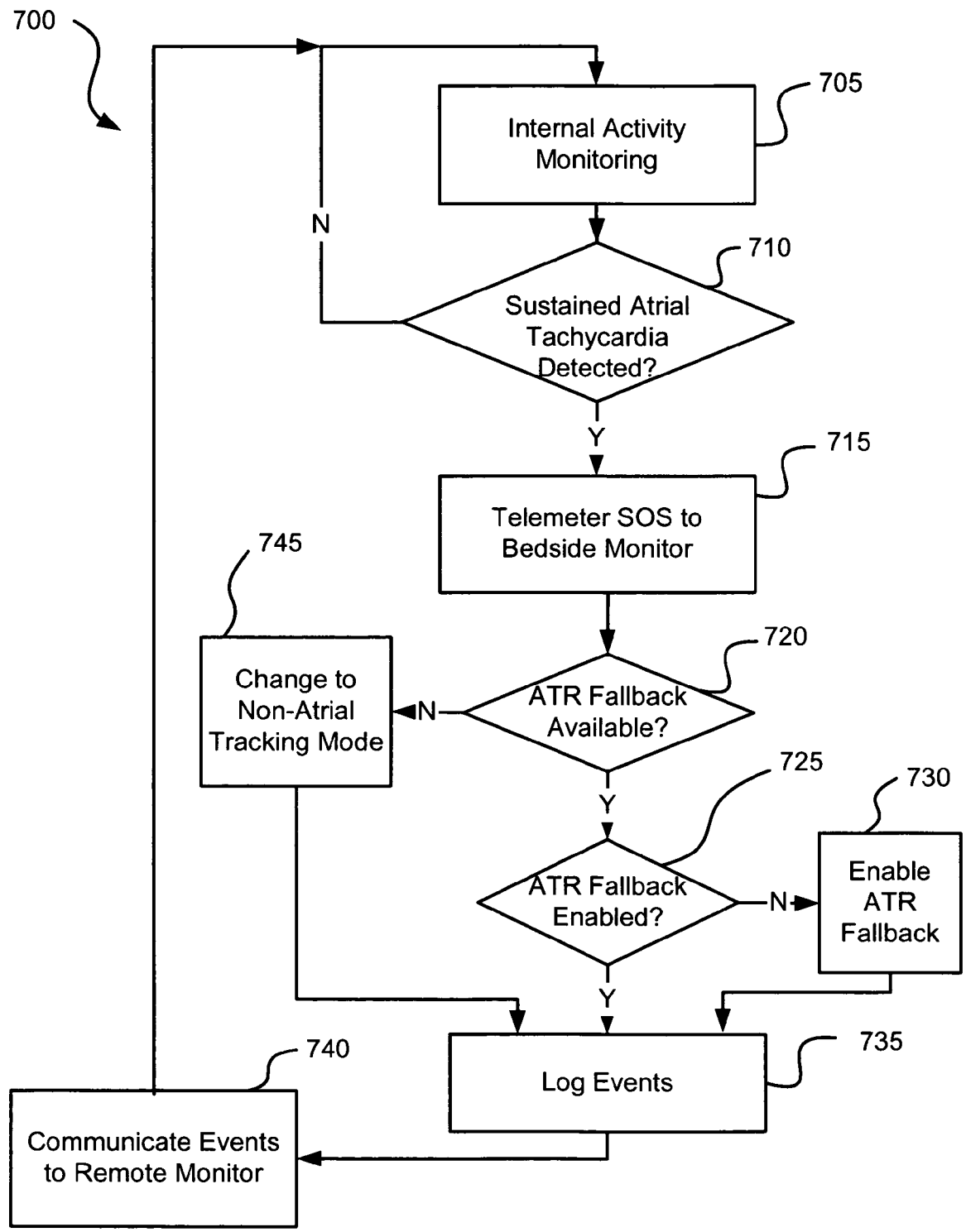
FIG. 7 is a flow diagram illustrating a method in accordance with some embodiments of the present invention for detecting atrial tachycardia and intervening therein.

Turning to FIG. 7, a flow diagram 700 illustrates a method in accordance with some embodiments of the present invention for detecting atrial tachycardia and intervening therein. Atrial tachycardia results in high ventricular pacing rate as the ventricle is paced in an effort to track runaway atrial events. Following flow diagram 700, activity monitoring is performed by a PG (block 705). Where the PG detects a sustained atrial tachycardia (block 710), an alarm or SOS signal is communicated to a bedside monitor (block 715). In addition, the monitor queries the PG to determined if ATR fallback is available (block 720). As may be appreciated by one of ordinary skill in the art, ATR fallback is a device feature that disassociates the device from the atrium so that pacing of the ventricle is based on something other than detection of the atrial signal. Such a feature can be used to prevent pacing the ventricle at the maximum rate during atrial tachycardia. Where ATR fallback is available (block 720), it is determined if it is enabled (block 725). Where ATR fallback is not enabled (block 725), it is changed by programming the PG to enable ATR fallback (block 730), and events surrounding the detected atrial fibrillation are logged (block 735) and communicated to a remote monitor (block 740).

Alternatively, where it is determined that ATR fallback is not available (block 720), the operational mode of the PG is changed to a non-atrial tracking mode (block 745). As may be appreciated by one of ordinary skill in the art, the non-atrial tracking mode is initiated by programming the PG to disso- ciate ventricular and atrial pacing, and thus allow the ventricular pacing rate to return to a more appropriate level. In addition, events surrounding the detected atrial fibrillation are logged (block 735) and communicated to a remote monitor (block 740).

The invention has now been described in detail for purposes of clarity and understanding. However, it will be appreciated that certain changes and modifications may be practiced within the scope of the appended claims. Thus, although the invention is described with reference to specific embodiments and figures thereof, the embodiments and figures are merely illustrative, and not limiting of the invention. Rather, the scope of the invention is to be determined solely by the appended claims.

What is claimed is:

1. A method for mitigating an apnea, the method comprising:
    determining if a patient is in a resting state;
    based at least in part on the resting state determination, generating an information signal indicating an occurrence of apnea;
    receiving the information signal from a deployed, implantable medical device at a local monitor;
    storing the information signal;
    associating a time stamp with the information signal;
    based at least in part on the information signal, autonomously selecting and initiating, by the local monitor, at least one appropriate therapy from among a plurality of available therapies for mitigating the occurrence of the apnea; and
    communicating a message based at least in part on the information signal and the time stamp to a remote monitor disposed beyond the telemetry range of the deployed, implantable medical device.

2. The method of claim 1, wherein the information signal is received via a wireless link.

3. The method of claim 2, wherein the local monitor is disposed within an external telemetry range of the deployed, implantable medical device, and wherein the remote monitor is disposed beyond the external telemetry range of the deployed, implantable medical device.

4. The method of claim 1, wherein communicating a message to a remote monitor includes transmitting information over a medium selected from a group consisting of a cellular telephone link, the Internet, a virtual private network, and a public switched telephone network.

5. The method of claim 1, wherein the therapy includes sounding an audible alarm.

6. The method of claim 1 wherein initiating a therapy includes programming the deployed, implantable device.

7. A method for mitigating an apnea, the method comprising:
    determining if a patient is in a resting state;
    based at least in part on the resting state determination, generating an information signal;
    receiving the information signal from a deployed, implantable medical device at a local monitor, the local monitor including diagnostics;
    indicating by the diagnostics an occurrence of apnea based at least in part on the information signal;
    storing the information signal;
    associating a time stamp with the information signal;
    based at least in part on the information signal, autonomously selecting and initiating, by the local monitor, at least one appropriate therapy from among a plurality of available therapies for mitigating the occurrence of the apnea; and communicating a message based at least in part on the information signal and the time stamp to a remote monitor disposed beyond the telemetry range of the deployed, implantable medical device.

8. The method of claim 7, wherein the information signal is received via a wireless link.

9. The method of claim 8, wherein the local monitor is disposed within an external telemetry range of the deployed, implantable medical device, and wherein the remote monitor is disposed beyond the external telemetry range of the deployed, implantable medical device.

10. The method of claim 7, wherein communicating a message to a remote monitor includes transmitting information over a medium selected from a group consisting of a cellular telephone link, the Internet, a virtual private network, and a public switched telephone network.

11. The method of claim 7, wherein the therapy includes sounding an audible alarm.

12. The method of claim 7 wherein initiating a therapy includes programming the deployed, implantable device.

* * * * *